United States Patent
Bogert (10) Patent No.: US 10,154,917 B2
(45) Date of Patent: Dec. 18, 2018

(54) HELICAL AND SEGMENTED STENT-GRAFT

(75) Inventor: David L. Bogert, Prescott, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 1867 days.

(21) Appl. No.: 12/666,158

(22) PCT Filed: Jun. 20, 2008

(86) PCT No.: PCT/US2008/067630
§ 371 (c)(1),
(2), (4) Date: Sep. 17, 2010

(87) PCT Pub. No.: WO2009/002827
PCT Pub. Date: Dec. 31, 2008

(65) Prior Publication Data
US 2011/0009951 A1    Jan. 13, 2011

Related U.S. Application Data

(60) Provisional application No. 60/936,890, filed on Jun. 22, 2007.

(51) Int. Cl.
*A61F 2/88* (2006.01)
*A61F 2/07* (2013.01)
*A61F 2/89* (2013.01)

(52) U.S. Cl.
CPC .......... *A61F 2/88* (2013.01); *A61F 2/07* (2013.01); *A61F 2/89* (2013.01); *A61F 2002/075* (2013.01); *A61F 2210/0076* (2013.01); *A61F 2220/005* (2013.01); *A61F 2220/0075* (2013.01); *A61F 2250/0036* (2013.01); *A61F 2250/0063* (2013.01)

(58) Field of Classification Search
CPC ........................................................ A61F 2/88
USPC ............................................... 623/1.13, 1.44
See application file for complete search history.

(56) References Cited

U.S. PATENT DOCUMENTS

| | | | |
|---|---|---|---|
| 4,955,899 A | 9/1990 | Della Coma et al. |
| 5,591,197 A | 1/1997 | Orth et al. |
| 5,667,523 A | 9/1997 | Bynon et al. |
| 5,824,040 A | 10/1998 | Cox et al. |
| 5,970,880 A | 10/1999 | Perotto |
| 6,042,605 A | 3/2000 | Martin et al. |
| 6,124,523 A | 9/2000 | Banas et al. |
| 6,264,684 B1 | 7/2001 | Banas et al. |
| 6,270,524 B1 | 8/2001 | Kim |
| 6,312,458 B1 | 11/2001 | Golds |
| 6,361,637 B2 | 3/2002 | Martin et al. |
| 6,398,803 B1 | 6/2002 | Layne et al. |

(Continued)

FOREIGN PATENT DOCUMENTS

WO    9837833 A1    9/1998

OTHER PUBLICATIONS

Jan. 16, 2009 International Search Report in international application No. PCT/US2008/067630 filed on Jun. 20, 2008.

(Continued)

*Primary Examiner* — Matthew Schall
(74) *Attorney, Agent, or Firm* — Rutan & Tucker, LLP (57) ABSTRACT

The stent-graft described herein generally includes a substrate, a helix disposed about the substrate, a covering disposed over at least a portion of the helix, and a support member coupled to the covering.

20 Claims, 2 Drawing Sheets

(56) References Cited

U.S. PATENT DOCUMENTS

| | | | |
|---|---|---|---|
| 6,494,904 B1* | 12/2002 | Love | A61F 2/07 623/1.1 |
| 6,520,986 B2 | 2/2003 | Martin et al. | |
| 6,558,414 B2 | 5/2003 | Layne | |
| 6,652,570 B2 | 11/2003 | Smith et al. | |
| 6,673,103 B1 | 1/2004 | Golds et al. | |
| 6,695,833 B1 | 2/2004 | Frantzen | |
| 6,712,844 B2 | 3/2004 | Pacetti | |
| 6,770,087 B2 | 8/2004 | Layne et al. | |
| 6,881,221 B2 | 4/2005 | Golds | |
| 6,911,040 B2 | 6/2005 | Johnson et al. | |
| 6,945,991 B1 | 9/2005 | Brodeur et al. | |
| 7,094,255 B2 | 8/2006 | Penn et al. | |
| 7,122,052 B2* | 10/2006 | Greenhalgh | A61F 2/07 623/1.13 |
| 7,147,660 B2 | 12/2006 | Chobotov et al. | |
| 7,169,175 B2 | 1/2007 | Cottone, Jr. et al. | |
| 7,351,255 B2 | 4/2008 | Andreas | |
| 2003/0229390 A1 | 12/2003 | Ashton et al. | |
| 2004/0024443 A1* | 2/2004 | Dwyer et al. | 623/1.13 |
| 2004/0167609 A1 | 8/2004 | Majercak | |
| 2004/0230288 A1 | 11/2004 | Rosenthal | |
| 2005/0278017 A1* | 12/2005 | Gregorich | 623/1.44 |
| 2006/0069424 A1 | 3/2006 | Acosta et al. | |
| 2006/0195175 A1 | 8/2006 | Bregulla | |
| 2008/0027534 A1* | 1/2008 | Edwin et al. | 623/1.44 |
| 2010/0324657 A1 | 12/2010 | Bogert | |

OTHER PUBLICATIONS

Jan. 16, 2009 Written Opinion of the ISA in international application No. PCT/US2008/067630 filed on Jun. 20, 2008.

Dec. 22, 2009 International Preliminary Report on Patentability in international application No. PCT/US2008/067630 filed on Jun. 20, 2008.

U.S. Appl. No. 12/666,031, filed Dec. 22, 2009 Non-Final Office Action dated Jul. 24, 2012.

PCT/US2008/067620 filed Jun. 20, 2008 International Preliminary Report on Patentability dated Dec. 22, 2009.

PCT/US2008/067620 filed Jun. 20, 2008 International Search Report dated Dec. 29, 2008.

PCT/US2008/067620 filed Jun. 20, 2008 Written Opinion dated Dec. 29, 2008.

* cited by examiner

HELICAL AND SEGMENTED STENT-GRAFT

PRIORITY

This application is a U.S. national stage application under 35 USC § 371 of International Application No. PCT/US2008/067630, filed Jun. 20, 2008, claiming priority to U.S. Provisional Patent Application No. 60/936,890, filed Jun. 22, 2007, each of which is incorporated by reference in its entirety into this application.

BACKGROUND

Intraluminal prostheses used to maintain, open, or dilate blood vessels are commonly known as stents. Stent constructions generally include lattice type cylindrical frames that define a plurality of openings. Common frameworks for stents include, for example, individual rings linked along the length of the stent by a linking member, a continuous helically wrapped member (that may include one or more linking members), a braid or a mesh formed into a tubular structure, and a series of interconnected struts. Stents may be formed by arranging one or more members in a pattern along a longitudinal axis to define essentially a cylinder and connecting the one or more members or otherwise affixing them in position (e.g., interconnecting with a filament). Stents may also be formed by cutting openings into a tube of material (e.g., shape memory).

Stents may have self-expanding and/or balloon expandable properties. Self-expanding stents are delivered to a blood vessel in a collapsed condition and expand in vivo following the removal of a constraining force and/or in the presence of an elevated temperature (due to material properties thereof), whereas balloon expandable stents are generally crimped onto a balloon catheter for delivery and require the outwardly directed force of a balloon for expansion. Stents can be made of various metals and polymers and can include a combination of self-expanding and balloon expandable properties.

Synthetic vascular grafts are routinely used to restore the blood flow in patients suffering from vascular diseases. For example, prosthetic grafts made from expanded polytetrafluoroethylene (ePTFE) are commonly used and have shown favorable patency rates, meaning that depending on a given time period, the graft maintains an open lumen for the flow of blood therethrough. Grafts formed of ePTFE include a microstructure characterized by spaced apart nodes connected by fibrils, the distance between the nodes defined as internodal distance (IND), and are generally extruded either as a tube or as a sheet or film that is fashioned into a tube. Grafts can also be created from fibers woven or knitted into a generally tubular shape.

It is known in the art to use stents in combination with vascular grafts to form stent-grafts. Because stent-grafts are often intraluminally deployed in vessels of varying sizes and tortuosity, flexibility can be an important consideration. Flexibility can be imparted to a stent-graft in a variety of ways, including, for example, connection of the stent to the one or more graft layers, configuration of the stent and/or graft layer(s), spacing of the stent struts, rings, or members along the length of the graft(s), etc. For example, U.S. Pat. No. 6,398,803 and U.S. Pat. No. 6,770,087 to Layne et al. describe a graft layer with openings to enhance flexibility. Another important consideration in the design of a stent-graft is the ability of the stent to withstand stress and fatigue, caused, for example, by plastic deformations occurring at strut junctions when the stent is subjected to circumferential forces. Stent strength can be enhanced through material choice, stent configuration, arrangement and configuration of graft layers, connecting members between stent members, etc. Another consideration in the design of certain stent-grafts is properties to resist kinking of the stent-graft. For example, when a stent-graft is positioned in a bend in a blood vessel or bypass graft, depending on the acuteness of the angle of the bend, the stent-graft can potentially kink and thereby become unsuitable for passage of blood therethrough.

One example of an allegedly flexible and kink resistant stent-graft is described in U.S. Pat. No. 6,042,605 to Martin et al., the stent-graft formed by helically arranging an undulating stent member about a graft member, interweaving a linking member between undulations in adjacent turns of the helical member, and helically arranging a coupling member in the form of a flat ribbon or tape around the assembly. Another example is provided in U.S. Pat. No. 6,312,458 to Golds, the stent-graft formed from an elongate wire helically wound about a graft member at a first angle and an elongate securement member helically wound over both the stent and graft members at a second angle not congruent to the first angle. Such a stent-graft is alleged to be an improvement over the Martin et al. stent-graft both because the use of a broad coupling member is said to decrease the overall flexibility of the stent-graft and because wrapping the coupling member at the same angular orientation of the stent is said to decrease flexibility and expandability of the stent. In each of these examples, however, the outermost layer is a thin tape, ribbon, thread or suture, rather than a support member, such that the radial strength of the stent-graft is limited.

The following references relate to stent-grafts: U.S. Pat. No. 5,667,523 to Bynon et al.; U.S. Pat. No. 6,042,605 to Martin et al.; U.S. Pat. No. 6,264,684 to Banas et al.; U.S. Pat. No. 6,312,458 to Golds; U.S. Pat. No. 6,361,637 to Martin et al., U.S. Pat. No. 6,398,803 to Layne et al.; U.S. Pat. No. 6,520,986 to Martin et al., U.S. Pat. No. 6,652,570 to Smith et al.; U.S. Pat. No. 6,673,103 to Golds et al.; U.S. Pat. No. 6,770,087 to Layne et al.; U.S. Pat. No. 6,881,221 to Golds; U.S. Pat. No. 6,911,040 to Johnson et al.; and U.S. Pat. No. 6,945,991 to Brodeur et al., each of which is incorporated by reference in its entirety into this application.

Applicants have recognized that it would be desirable to provide a stent-graft that is able to combine flexibility, kink-resistance and good radial strength, embodiments of which are described herein along with methods of making same.

BRIEF SUMMARY

Accordingly, a strong, flexible stent-graft is described herein. In one embodiment, an implantable prosthesis includes a generally tubular substrate, a helix disposed about an outer surface of the substrate along a longitudinal axis, the helix having a first thickness, a covering disposed over at least a portion of the helix, and a support member coupled to an outer surface of the covering, the support member having a second thickness greater than the first thickness.

In another embodiment, a stent-graft includes a helix disposed about a substrate, the helix having a first thickness, a covering disposed over at least a portion of the helix, and a support member coupled to the covering, the support member having a second thickness greater than the first thickness. In another embodiment, a stent-graft includes a helix disposed about a substrate, the material of the helix having a first stiffness, a covering disposed over at least a portion of the helix, and a support member coupled to the covering, the support member material having a second stiffness greater than the first stiffness.

In yet another embodiment, a stent-graft includes a helix disposed about a substrate, a covering disposed over at least a portion of the helix, and two or more expandable segments coupled to the covering, adjacent expandable segments spaced at least about 3 mm from each other. In still another embodiment, a stent-graft includes a self-expanding helix disposed about an ePTFE substrate, a covering disposed over at least a portion of the helix, and a plurality of spaced apart expandable segments coupled to the covering.

In one embodiment, a method of making a stent-graft includes winding an elongate member, having a first thickness, about a generally tubular substrate to form a helix, disposing a covering over at least a portion of the helix, bonding the covering to at least one of the substrate and helix, and coupling a support member, having a second thickness greater than the first thickness, to the covering.

These and other embodiments, features and advantages will become more apparent to those skilled in the art when taken with reference to the following more detailed description in conjunction with the accompanying drawings that are first briefly described.

DESCRIPTION OF THE PREFERRED EMBODIMENTS

The following description should be read with reference to the drawings, in which like elements in different drawings are identically numbered. The drawings, which are not necessarily to scale, depict selected embodiments and are not intended to limit the scope of the invention. The description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment. In addition, the term "thickness" used with respect to a structural feature (e.g., helix, support member, stent, etc.) indicates a distance from a first side of the structure to a second side of the structure, where the first side may be adjacent and/or coupled to an underlying member (e.g., a substrate, covering, graft, layer, etc.), and where the second side may be adjacent and/or coupled to an overlying member (e.g., a covering, graft, layer, etc.).

The implantable prosthesis (e.g., stent-graft) described herein includes a substrate that forms a smooth inner luminal surface for the prosthesis, a helix disposed about the substrate, a covering disposed over at least a portion of the helix, and a support member coupled to the covering. The combination of a helix and support member (e.g., with spaced apart expandable segments) overcomes issues that are prevalent in certain stent-grafts lacking such a combination. For example, segmented stent-grafts (e.g., stent-grafts having a structure of disconnected expandable segments) are known to suffer from subduction, a condition known by those skilled in the art as a "Z-kink" because the stent-graft forms a "Z" shape when adjacent segments become offset from one another with respect to the longitudinal axis of the stent-graft. Stent-grafts including a graft material with a relatively thin wall are also known to suffer from billowing of the graft material into the inside surface or the lumen of the stent-graft when deployed. Billowing may occur when the stent-graft is positioned in an undersized vessel (e.g., artery) and is characterized by substantially non-uniform radial expansion of the stent-graft. Utilizing a helix mitigates subduction and billowing issues and also imparts excellent flexibility, fatigue life and kink-resistance to the stent-graft. However, the helix alone without a support member suffers from a lack of radial strength. Thus, the stent-graft described herein, including both a helix and support member, enjoys a combination of advantageous features that are beneficial to the life and effectiveness of the stent-graft.

In one embodiment, the substrate has a thickness generally in the range of approximately 10 microns to approximately 200 microns, and preferably in the range of approximately 20 microns to approximately 80 microns. The substrate is generally flexible and compressible. Potential materials for the substrate include, for example, expanded polytetrafluoroethylene (ePTFE), polyester, polyurethane, fluoropolymers, polytetrafluoroethylene, silicones, urethanes, ultra high molecular weight polyethylene, aramid fibers, and combinations thereof. One preferred embodiment for a substrate material is ePTFE. The node-fibril microstructure of an ePTFE substrate may include various orientations for the fibrils, but in a preferred embodiment, the fibrils are oriented generally parallel to the longitudinal axis of the substrate. The average internodal distance (IND) for one preferred embodiment of a substrate and/or covering described herein is in the range of approximately 6 microns to approximately 80 microns. Also, as described in U.S. Pat. No. 5,790,880 to Banas et al., which is incorporated by reference in its entirety in this application, the substrate and/or covering may be made of an ePTFE that undergoes nodal elongation during radial expansion. An ePTFE substrate may be manufactured in a number of ways, including, for example, extrusion of a tube (seamless), extrusion of a sheet that is subsequently formed into a tube (one or more seams), helical wrapping of ePTFE tape around a mandrel (e.g., multiple seams or preferably a single helical seam), etc.

The stent-graft described herein may be utilized with bio-active agents. Bio-active agents can be coated onto a portion or the entirety of the stent-graft, substrate, and/or covering for controlled release of the agents once the prosthesis is implanted. The bio-active agents can include, but are not limited to, vasodilator, anti-coagulants, such as, for example, warfarin and heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; anti-proliferative/ antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/ antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The helix and/or support member in one embodiment may be formed of a shape memory material, including, for example, shape memory metals, shape memory alloys, super elastic shape memory metal alloys, linear elastic shape memory alloy, metal alloys, shape memory polymers, polymers, bio-resorbable material, and combinations thereof. One preferred shape memory material is Nitinol, while another is a cobalt chrome alloy. The helix and/or support member may also be formed of metal, such as, for example, stainless steel, platinum, and Elgiloy, or certain polymers. Moreover, portions of the helix and/or support member may be made of a bio-resorbable material. As used herein, the term "bio-resorbable" includes a suitable bio-compatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above. Potential materials for the prosthesis described herein include, for example, biodegradable polymers such as polylactic acid, i.e., PLA, polyglycolic acid, i.e., PGA, polydioxanone, i.e., PDS, polyhydroxybutyrate, i.e., PHB, polyhydroxyvalerate, i.e., PHV and copolymers or a combination of PHB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes.

The helix may be connected to the substrate by various methods, which can be facilitated by the material selection for the helix, substrate and/or coatings, if utilized. An adhesive, a polymer bonded by a solvent, sutures, or other methods may be used to connect the helix to the substrate. Other alternatives known in the art are additionally within the scope of the invention, including weaving the substrate around the helix. The substrate may additionally be longitudinally compressed before connecting the helix thereto. The substrate is compressed from a first length to a second length, which is approximately 50% to about 97% of the first length. Longitudinal compression of an ePTFE graft is described in U.S. Pat. No. 4,955,899 to Della Corna et al. and is incorporated by reference in its entirety in this application. In one embodiment, an adhesive may be disposed between the helix and the substrate to bond the helix to the substrate. Suitable biocompatible bonding agents may include polytetrafluoroethylene, polyurethane, polyethylene, polypropylene, polyamides, polyimides, polyesters, polypropylenes, polyethylenes, polyfluoroethylenes, silicone fluorinated polyolefins, fluorinated ethylene/propylene copolymer, perfluoroalkoxy fluorocarbon, ethylene/tetrafluoroethylene copolymer, and polyvinylpyrolidone. The bonding agent may constitute an interfacial layer between the helix and the substrate, or may be a polymeric cladding at least partially concentrically surrounding the helix.

In another embodiment, a polymer may be applied to the helix, and a solvent applied over the helix to bond the helix to the substrate. A suitable solvent may be an aprotic solvent including dimethylacetamide (DMSE), dimethylforamide, THF, or their mixtures. For example, in one embodiment a generally tubular ePTFE substrate is positioned over a mandrel. The substrate may be sintered, unsintered, or partially sintered. The helix with a polyurethane coating over at least a portion of its length is positioned along the outer surface of the ePTFE substrate. Once the helix is initially positioned on a surface of the substrate, a laser alignment fixture is optionally utilized to optimally space the adjacent windings of the helix with respect to one another. The mandrel is then removed from the assembly and a solvent, such as tetrahydrofuran (THF), is applied to the inside surface of the ePTFE substrate, so that the THF migrates through the wall of the ePTFE substrate. The interaction between the ePTFE, THF and polyurethane coating on the helix bonds the helix to the ePTFE substrate (the THF or other aprotic solvent is believed to dissolve polyurethane, such that when a small amount contacts the polyurethane coating, a mechanical bond is developed between the coating and the ePTFE substrate).

Markers M1, M2, M3, M4 . . . Mn can be provided for all of the embodiments described herein. The marker Mn can be formed from the same material as the stent as long as the material is radiographic or radiopaque. The marker material can also be formed, for example, from gold, tantalum, platinum, and combinations thereof. One or more markers can be formed from a marker material different from other markers.

Figure 1:
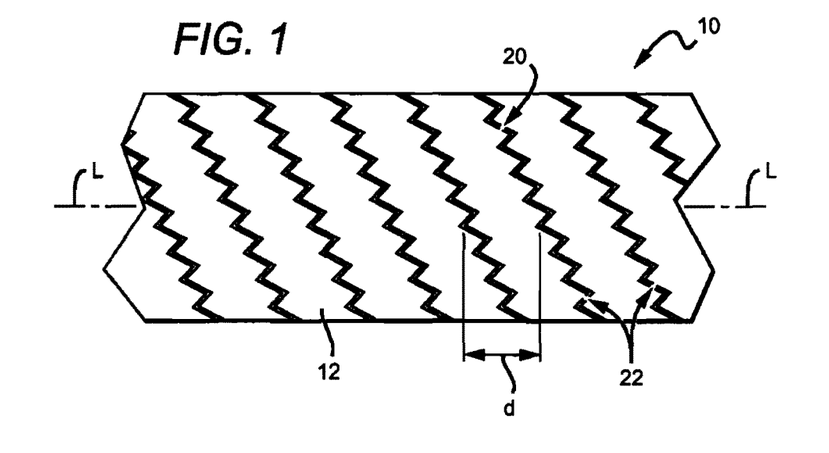
FIG. 1 is a partial side view of a helix disposed about a substrate.

Referring now to FIG. 1, a stent-graft 10 is illustrated, including a substrate 12 and a helix 20. The helix 20 is formed in a preferred embodiment by helically winding one or more elongate members about a longitudinal axis to form spaced apart helical windings 22. The helix 20 is disposed about an outer surface of the substrate 12 such that adjacent helical windings 22 are spaced a distance d from one another. In one embodiment, the distance d between adjacent helical windings of helix 20 is approximately equal along the substrate 12, a preferred distance d in the range of about 5% to about 10% of the outside diameter of the stent-graft. In other embodiments, the distance between adjacent helical windings 22 may be varied along the length of the substrate 12. For example, beginning at one end of the substrate 12, the distance between the first two helical windings, d1, could be less than the distance d2 between subsequent helical windings. The distance between adjacent helical windings could then progressively become greater along the length of the stent-graft, could alternate between d1 and d2, could be progressively smaller toward a mid-section of the substrate, could be different along a mid-region of the substrate than at the first and second ends thereof, etc. In embodiments in which the helix 20 includes two or more elongate members, the members could be helically wound about the substrate in different directions and/or with different helical angles. In certain embodiments, the helix 20 is formed prior to positioning over the substrate. In other embodiments, an elongate member is helically wound about the outer surface of the substrate. In some embodiments, the helix 20 is placed under tension as it is disposed about the substrate.

In one embodiment, the helix 20 includes struts arranged in a zig-zag configuration as shown in FIG. 1. The struts intersect at an apex to form a first set of apices and a second set of apices offset therefrom. Each apex includes a peak and a trough. The lengths of the struts may be uniform, as shown, or may be varied about the length of the one or more elongate members forming the helix. In addition to zig-zag configurations, other configurations are also possible and within the scope of the invention, such as, for example, sinusoidal patterns, meandering curve patterns, other curvilinear patterns, etc. The struts may be substantially straight along their lengths, as shown, or may be curved or wave-like. The wave-like pattern can be generally sinusoidal in that the pattern may have the general form of a sine wave, whether or not such wave can be defined by a mathematical function. Alternatively, any wave-like forms can be employed so long as it has amplitude and displacement. For example, a square wave, saw tooth wave, or any applicable wave-like pattern defined by the struts where the struts have substantially equal lengths or unequal lengths. Any type of pattern and/or strut length or shape can be combined with other patterns and/or strut lengths or shapes to form a non-uniform helix. Moreover, it should be appreciated that the shape, size, thickness, material and/or other characteristic of the one or more elongate members forming the helix can be varied along the length thereof.

In one embodiment, the helical windings 22 of the helix 20 are positioned along a surface of the substrate 12 so that the peak of the apices on one helical winding is aligned with a trough of the apices on an adjacent helical winding, the adjacent windings spaced apart a sufficient distance d to prevent interference between the windings upon radial compression of the stent-graft. For example, the helix 20 may be coupled to the substrate 12 in an expanded configuration defining an expanded perimeter of the helix 20 and subsequently radially compressed to a collapsed configuration, defining a collapsed perimeter of the helix 20 smaller than the expanded perimeter. In another embodiment, the distance d between adjacent helical windings 22 is such that regardless of alignment, radial compression of the helix will not result in interference between adjacent helical windings 22 (e.g., interlocking of the struts). The distance d between adjacent windings 22 can be varied as discussed above to impart to the stent-graft 10 a preferable characteristic. For example, a relatively small distance d may impart greater structural strength to the stent-graft, while a relatively large distance d may impart greater flexibility to the stent-graft. The struts of the helix 20 may be approximately equivalent in length, as shown in FIG. 1, or may have different lengths. For example, in one embodiment a longer first strut and a shorter second strut alternate along the length of the one or more elongate members forming the helix. The first strut and second strut intersect at an apex to form a first angle $\Phi$ between the first and second struts. The bisection of first angle $\Phi$ by a line parallel to the longitudinal axis L of the stent-graft results in two substantially equivalent second and third angles $\theta$.

Figure 2:
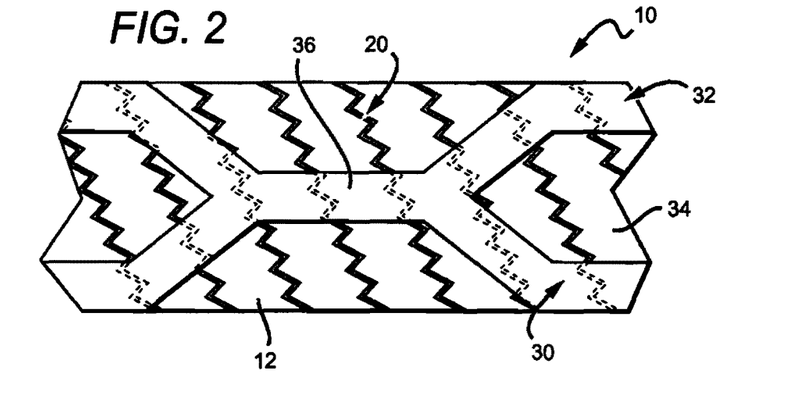
FIG. 2 is a partial side view of covering disposed over a portion of the helix and substrate of FIG. 1.

In a preferred embodiment, a covering is disposed about the substrate and helix, as shown in FIG. 2. The covering may include, for example, a continuous member disposed lengthwise from a first end to a second end of the substrate and/or the helix (elongate member helically wound about the longitudinal axis, a tube with patterned cutouts, etc.), one or more individual members spaced apart or intersecting along the length of the substrate and/or helix, a combination thereof, etc. In one embodiment, the covering is a continuous ePTFE member with a "lacey" graft configuration, and in another embodiment is a continuous ePTFE member with a plurality of slits, such as or similar to that described in U.S. Pat. No. 6,398,803 and U.S. Pat. No. 6,770,087 to Layne et al. With respect to a covering that includes slits, the slits may be relatively small such that several slits may be arranged along the covering. The slits may be arranged generally perpendicular to the longitudinal axis of the covering (e.g., longitudinally adjacent slits aligned, circumferentially offset, a combination thereof, etc.), generally parallel to the longitudinal axis of the covering (e.g., circumferentially adjacent slits aligned, longitudinally offset, a combination thereof, etc.), or some combination thereof. Alternatively, the slits may extend over a majority of the distance longitudinally or circumferentially of the graft member, depending on arrangement.

Referring to FIG. 2, the stent-graft 10 includes a covering 30 disposed over at least a portion of the helix 20. The covering 30 has a generally tubular shape and is configured in a honeycomb-type pattern or lattice structure, including a plurality of cells 32 with each cell 32 having a central opening 34. The central opening 34 has a hexagon shape in the embodiment shown, although other geometric shapes, including polygonal shapes, are possible and within the scope of the invention. The cells 32 are connected together via links 36, which in one embodiment act as hinges, having a point of pivot to permit rotational pivoting motion thereof. In one embodiment, the links 36 are arranged in spaced apart sets of two, the first link in a given set positioned circumferentially approximately 180 degrees apart from the second link, and adjacent sets of links are rotated approximately 90 degrees from one another. Thus, for example, links 36, which are arranged approximately parallel to the longitudinal axis L and are therefore noted as longitudinal links, connect adjacent cells 32 in a first row of cells and adjacent cells 32 in a second row of cells located opposite the first row of cells (spaced circumferentially approximately 180 degrees therefrom). Links that are arranged approximately perpendicular to the longitudinal axis L, circumferential links (not shown), are rotated approximately 90 degrees with respect to longitudinal links 36 and connect each cell 32 in the first row of cells with its circumferential counterpart in the second row of cells in two locations spaced approximately 180 degrees apart (i.e., first row cells are connected to second row cells at approximately the same axial position along the longitudinal axis by two circumferential links).

Figure 3:
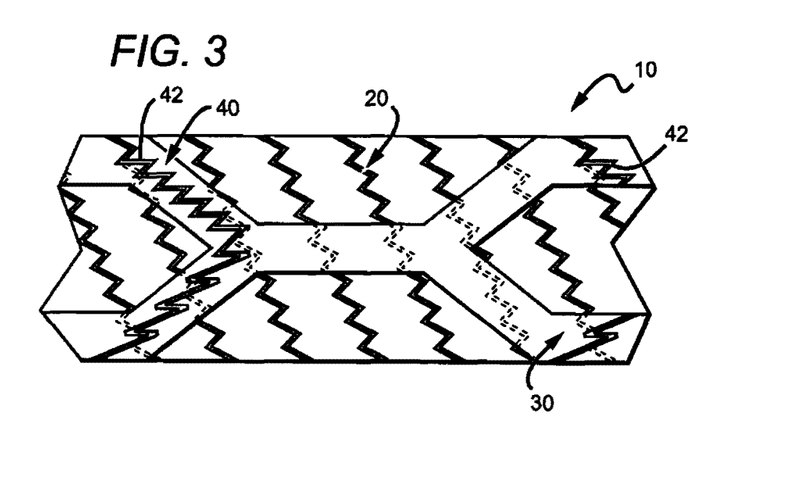
FIG. 3 is a partial side view of one embodiment of a stent-graft, including a support member coupled to an outer surface of the covering of FIG. 2.

In FIG. 3, the stent-graft 10 includes a support member 40 coupled to an outer surface of the covering 30. The support member 40 in one embodiment includes a plurality of expandable segments in the form of discrete circumferential sections 42 spaced along a surface of the covering. In other embodiments, the expandable segments of the support member may include other stent configurations, such as, for example, windings of an elongate continuous member helically disposed about the covering, interconnected annular members disposed over the covering, combinations of the embodiments described, etc. The circumferential sections 42 may include a plurality of connected struts having a zig-zag configuration as shown or any type of stent configuration, including those discussed above.

In one embodiment the support member 40 has a thickness generally greater than the thickness of the helix such that the support member is more stiff than the helix. For instance, in an embodiment in which each of the helix and support member have a generally uniform thickness, the thickness of the helix is less than the thickness of the support member (or at least less than one or more expandable segments of the support member). In an embodiment in which the helix and/or support member have a varying thickness (e.g., the elongate member(s) forming the helix have a thickness that increases along a certain section, expandable segments of a support member are thicker along certain sections of the stent graft, one or more expandable segments of the support member have a varying thickness, etc.), the thickest portion of the helix is less than the thinnest portion of the support member. In one embodiment, the thickness of the helix is in the range of about 50 microns to about 1000 microns and the thickness of the support member is in the range of about 0.5 mm to about 2.0 mm. Other configurations may also result in the support member being more stiff than the helix. For example, in one embodiment, the support member struts have a width greater than the width of the helix struts. In another embodiment, the support member is more stiff than the helix due to differences in the material thereof. Thus, for example, the struts or portions of the support member could be less thick and/or wide than the struts or portions of the helix, while imparting a stiffness to the support member greater than the stiffness imparted to the helix by its struts or portions. In one embodiment, the helix has struts that are wider and/or thicker than the struts of the support member, but the helix is formed from a soft biodegradable polymer while the support member is formed from a hard stainless steel.

In addition, the distance D that the expandable segments of the support member are spaced from one another along the longitudinal axis can be manipulated to achieve a desired combination of flexibility and radial strength. For example, in an embodiment in which greater flexibility is desired, the distance D is greater than that of an embodiment in which greater radial strength is desired. In one embodiment, adjacent expandable segments are spaced at least about 3 mm from each other. It should be appreciated that the spacing between expandable segments of the support member, as well as the thickness/width and material differential between the helix and support member, permit the tailoring of the stent-graft to achieve an advantageous combination of flexibility and radial strength, depending on the desired application.

Figure 4:
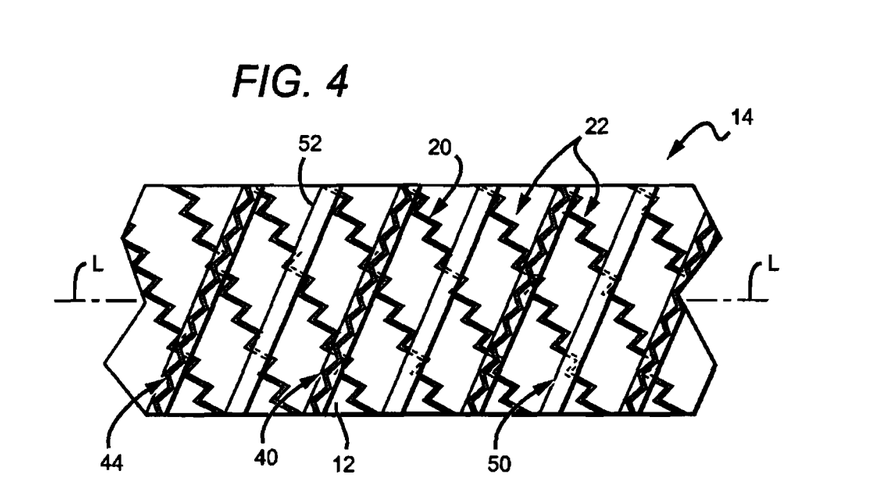
FIG. 4 is another embodiment of a stent-graft, the covering including an elongate strip helically disposed about a helix and substrate.

FIG. 4 illustrates an embodiment of a stent-graft 14 with a helix 20 disposed about an outer surface of a substrate 12, the windings 22 of the helix forming generally a first angle with respect to the longitudinal axis L (however, it should be appreciated that all of the windings 22 may not form precisely the same angle and that angle variation along the longitudinal axis L is contemplated for certain embodiments). A covering 50 includes an elongate strip of material (e.g., ePTFE) that is helically wound about the longitudinal axis L to create helical windings 52 that form generally a second angle with respect to the longitudinal axis L different from the first angle. For instance, in the embodiment shown, each of the first and second angles are generally oblique, one forming an acute angle and the other forming an obtuse angle, although in other embodiments each angle is generally acute (or obtuse). A support member 40, including spaced apart circumferential sections 44, is coupled to the outer surface of the covering 50 such that a winding 52 without a circumferential section 44 coupled thereto is disposed between adjacent circumferential sections 44. In some embodiments, each winding 52 of the covering has a circumferential section or other expandable segment of the support member coupled to an outer surface thereof, while in other embodiments, two or more windings 52 without an expandable segment of the support member are disposed between adjacent expandable segments (e.g., circumferential sections).

Figure 5:
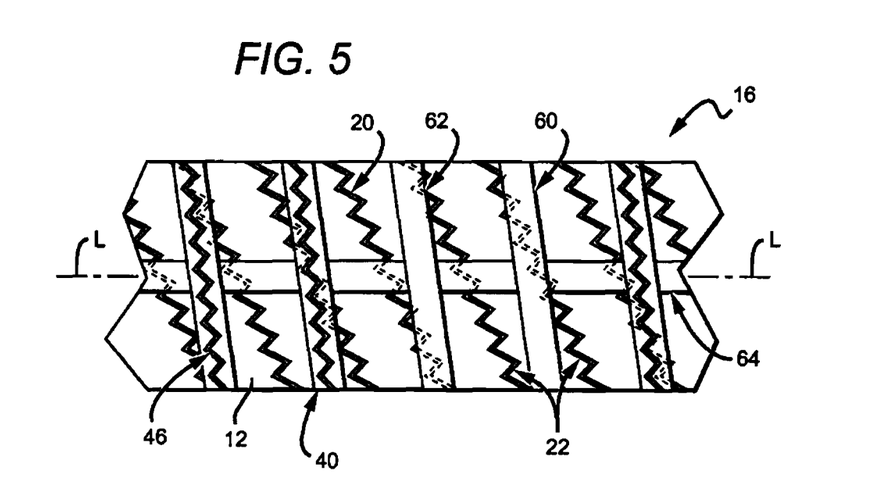
FIG. 5 is another embodiment of a stent-graft, the covering including spaced apart rings disposed about a helix and substrate.

FIG. 5 shows an embodiment of a stent-graft 16 with a helix 20 disposed about an outer surface of a substrate 12. A covering 60, including spaced apart annular rings 62 and one or more longitudinal strips 64, are disposed over portions of the helix 20 and substrate 12. The annular rings 62 may form an oblique angle with the longitudinal axis L, as shown, or may be disposed generally perpendicular to the longitudinal axis L. The longitudinal strip(s) 62 are disposed transverse to the annular rings 62 and, as shown, generally parallel to the longitudinal axis L, although in some embodiments, the longitudinal strips also form an oblique angle with the longitudinal axis L. A support member 40, including a plurality of circumferential sections 46, is coupled to the covering 60 by coupling circumferential sections 46 to the outer surface of select annular rings 62 in a predetermined pattern. For example, as shown, the pattern is two adjacent circumferential sections 46 attached to two adjacent annular rings 62, followed by two adjacent annular rings 62 without a circumferential section 46, etc. Of course, other patterns, such as those discussed above, are also possible and within the scope of the invention. The longitudinal strip(s) 64 may be disposed over the helix 20 prior to the disposition of the annular rings 62, subsequent to the disposition of the annular rings 62 and/or support member, or during the disposition of the annular rings 62 in any woven-type pattern (e.g., the longitudinal strip 64 may be alternately disposed under an annular ring 62 and over an adjacent annular ring). The longitudinal strips 64 may be placed under tension during disposition thereof. Other embodiments of stent-grafts with strips and bands are set forth in U.S. Pat. No. 6,558,414 to Layne, which is incorporated by reference in its entirety in this application.

The coverings 50, 60 in FIGS. 4 and 5 are preferably made of ePTFE and, respectively, can be attached to an underlying ePTFE substrate 12 through the application of heat and/or pressure, and/or other methods, as described, for example, in U.S. Pat. No. 6,124,523 to Banas et al., which is incorporated by reference in its entirety in this application. Adhesives and/or solvents may also be used instead of, or in conjunction with, the aforementioned attachment methods. For example, a polymer coating (e.g., a urethane resin, silicone, FEP, combinations thereof, etc.) could be disposed on sides of the helix 20 to contact both the substrate and the covering when assembled together. Thereafter, the assembly can be soaked in a solvent for bonding. Also, the helix 20 could be sutured to the substrate at various locations along the length thereof. In one embodiment, the substrate 12 is initially unsintered ePTFE and is located over a mandrel for positioning of the helix 20 and covering, which may be sintered or partially sintered. The assembly is then heated to sinter the substrate to the covering (e.g., 360 degrees C. for 10 minutes). Prior to heating, the assembly may be subject to pressures to force the separate layers together (e.g., by wrapping with a tape). The support member may be coupled to the covering during or after this process.

In one embodiment, the materials for the stent-graft include ePTFE for the substrate, shape memory material for the helix and support member, and a covering knitted or woven with high strength polymer fibers such as ultra high molecular weight polyethylene fibers (e.g., Spectra®, Dyneema Purity®, etc.) or aramid fibers (e.g., Technora®, etc.). In one method of assembly, the substrate is positioned over a mandrel and the helix 20 is located thereover. The covering is then disposed over the helix, accordingly positioned with respect to the helix and substrate, and placed under tension (e.g., proximal and distal ends of the covering are pulled in opposite directions) and clamped or otherwise fixed in place. The stent-graft 60 in its assembled form is then preferably contacted with a polymeric adhesive, such as polyurethane, to bond the covering to the helix and/or the substrate. Optionally, the polymeric adhesive can be activated by a solvent, such as tetrahydrofuran (THF). Other modes of attachment (e.g., resin, sutures, heat, pressure, etc.) may also be used in conjunction with the solvent to assist in bonding. Adhesives and/or solvents, as discussed above, may also be used to couple the support member to the covering while the helix is being bonded to the covering and/or substrate or at some point thereafter.

In certain embodiments, the helix and support member include a self-expanding material and are arranged over the substrate in an expanded configuration defining an expanded perimeter of the stent-graft. In one embodiment of treating a blood vessel, a stent-graft including a self-expanding helix and support member is first compressed, the helix and support member collapsing to a collapsed configuration with a collapsed perimeter smaller than the expanded perimeter. A constraining sheath, which may be a component of a delivery system, is positioned over the stent-graft to maintain the helix and support member in the collapsed configuration and the sheath is delivered intraluminally in a patient to a predetermined region of a blood vessel. The constraining sheath is then removed from the stent-graft, allowing the helix and support member to expand. A balloon can optionally be inserted and inflated thereafter to ensure contact of the stent-graft with the blood vessel wall and positioning of the stent-graft in the blood vessel. In other embodiments, the helix and/or support member include a balloon expandable material and are arranged over the substrate in an original or non-expanded configuration with a original perimeter. In one embodiment of treating a blood vessel, a stent-graft including a balloon expandable helix and/or support member is positioned over a length of a balloon on a balloon catheter, which may be a component of a delivery system (e.g. the balloon catheter may be coaxially disposed in an outer sheath). The balloon catheter/delivery system is inserted intraluminally in a patient to a predetermined region of a blood vessel and the balloon is then inflated to expand the stent-graft, the helix and support member expanding to an expanded configuration with an expanded perimeter larger than the original perimeter. After positioning is confirmed, the balloon is deflated and the balloon catheter removed from the blood vessel. The helix and support member, whether balloon-expandable, self-expandable, or a combination thereof, may include a bio-resorbable material, as set forth above.

The invention has been described and specific examples have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. An implantable prosthesis, comprising:
   a generally tubular substrate;
   a helix disposed over an outer surface of the substrate along a longitudinal axis, the helix having a first thickness;
   a covering separate from the tubular substrate disposed over at least a portion of the helix; and
   a support member coupled to an outer surface of the covering, the support member having a second thickness greater than the first thickness and overlapping at least a portion of the helix.

2. The implantable prosthesis according to claim 1, wherein the helix comprises a continuous member helically disposed along a longitudinal axis from a first end to a second end to define a plurality of spaced apparat helical windings that are not interconnected.

3. The implantable prosthesis according to claim 2, wherein a space between helical windings at the first end and the second end is different from a space between helical windings along a mid-region of the generally tubular substrate when the implantable prosthesis is in a relaxed condition.

4. The implantable prosthesis according to claim 1, wherein the generally tubular substrate and covering comprise ePTFE.

5. The implantable prosthesis according to claim 4, wherein the covering is an elongate strip of material arranged helically over the helix.

6. The implantable prosthesis according to claim 5, wherein the helix is disposed about the generally tubular substrate at a first angle with respect to the longitudinal axis and the elongate strip of material is disposed about the helix at a second angle with respect to the longitudinal axis different from the first angle.

7. The implantable prosthesis according to claim 4, wherein the covering comprises a plurality of annular rings, which are not interconnected, spaced apart along the longitudinal axis.

8. The implantable prosthesis according to claim 7, further comprising at least one elongate strip of ePTFE material arranged generally parallel to the longitudinal axis.

9. The implantable prosthesis according to claim 1, wherein the covering comprises ultra high molecular weight polyethylene fibers woven or knitted into a network of cells and links.

10. The implantable prosthesis according to claim 9, wherein the network of cells and links includes a central opening defining a hexagonal shape.

11. The implantable prosthesis according to claim 9, wherein the network of cells are arranged along the longitudinal axis in a first row and a second row spaced circumferentially approximately 180 degrees from the first row.

12. The implantable prosthesis according to claim 11, wherein adjacent cells along the first row are connected by a longitudinal link and adjacent cells along the second row are connected by a longitudinal link.

13. The implantable prosthesis according to claim 12, wherein the first row cells are connected to the second row cells at approximately the same axial position along the longitudinal axis by a first circumferential link and a second circumferential link spaced approximately 180 degrees from the first circumferential link.

14. The implantable prosthesis according to claim 13, wherein the first and second circumferential links are rotated approximately 90 degrees with respect to the longitudinal links.

15. The implantable prosthesis according to claim 1, further comprising a polymeric adhesive disposed over at least a portion of the helix and a tetrahydrofuran (THF) solvent disposed over at least a portion of the covering.

16. The implantable prosthesis according to claim 1, wherein the first thickness is in a range of about 50 microns to about 1000 microns, and wherein the second thickness is in a range of about 0.5 mm to about 2.0 mm.

17. The implantable prosthesis according to claim 1, wherein the support member is disposed substantially coincident with the outer surface of the covering.

18. The implantable prosthesis according to claim 1, wherein the support member is disposed substantially coincident with the covering outer surface.

19. A stent-graft, comprising:
a helix disposed over an outer surface of a substrate, a material of the helix having a first stiffness;
a covering separate from the substrate and disposed over at least a portion of the helix; and
a support member coupled to the covering, a material of the support member having a second stiffness greater than the first stiffness and overlapping at least a portion of the helix.

20. A stent-graft, comprising:
a self-expanding helix disposed over an outer surface of an ePTFE substrate;
a covering separate from the ePTFE substrate and disposed over at least a portion of the helix; and
a plurality of spaced apart expandable segments coupled to the covering and overlapping at least a portion of the helix.

* * * * *